United States Patent [19]

Nakagawa et al.

[11] Patent Number: 4,958,029

[45] Date of Patent: Sep. 18, 1990

[54] PROCESS FOR THE PRODUCTION OF ISOINDOLINE DERIVATIVES, NOVEL INTERMEDIATES AND PROCESS FOR THEIR PRODUCTION

[75] Inventors: Susumu Nakagawa, Okazaki; Satoshi Murase, Nagoya; Ryosuke Ushijima; Yoshiaki Kato, both of Okazaki, all of Japan

[73] Assignee: Banyu Pharmaceutical Co., Ltd., Tokyo, Japan

[21] Appl. No.: 140,996

[22] Filed: Jan. 5, 1988

[30] Foreign Application Priority Data

Jan. 13, 1987 [JP] Japan .................................. 62-5643
Jan. 13, 1987 [JP] Japan .................................. 62-5644

[51] Int. Cl.⁵ .................. C07D 209/58; C07D 209/44
[52] U.S. Cl. ..................................... 548/430; 548/482
[58] Field of Search ............................... 548/482, 430

[56] References Cited

U.S. PATENT DOCUMENTS 3,084,167  4/1963  Rice ..................................... 548/482
4,064,139  12/1977  Anderson et al. .................. 548/425
4,677,100  6/1987  Nakagawa et al. ................. 540/222

FOREIGN PATENT DOCUMENTS 0186187  7/1986  European Pat. Off. .
2270864  12/1975  France .

OTHER PUBLICATIONS

A. Babayan et al., Chemical Abstracts, vol. 74, No. 53389t (1971).
J. Pharm., Sci. (1964), vol. 53, pp. 981–982, "Facile Synthesis of Isoindoline and Substituted Isoindolines", J. L. Neumeyer.
J. Org. Chem. (1954), vol. 19, pp. 884–893, "N-Alkyl Imides and Their Reduction by Means of Lithium Aluminum Hydride", L. M. Rice et al.
J. Org. Chem. (1975), vol. 40, pp. 957–958, "On the Specificity of Amine Solvation", F. M. Menger et al.
J. Am. Chem. Soc. (1953), vol. 77, pp. 616–621, "Hypotensive Agents, V.¹ Hydrogenated Bis-Isoindole Quaternary Salts²", L. M. Rice et al.
J. Chem. Soc. (1953), vol. 77, pp. 612–618, "Indoles, Part III,* The Action of (A) Ozone, and (B) Osmium Tetroxide on Some Indole Derivatives", D. Ockenden et al.
J. Chem. Soc. (1957), vol. 79, pp. 3165–3172, "The Chemotherapy of Filariasis, Analogues of Diethylcarbamazine (1-Diethylcarbamoyl-4-Methylpiperazine), derived from 2:4'– and 4:4'– Dipiperidyl, Homopiperazine, and 4-Aminopiperidine", P. Brooks et al.
J. Am. Chem. Soc. (1953), vol. 79, pp. 3167–3174, "Tetrachloroisoindolines and Related Systems, Alkylation Reactions and Inductive Effects", W. Rosen et al.
Org. Synth., Coll., vol. 5, pp. 406–408, "1,3-Dihydroisoindole", J. Bornstein et al.
Org. Synth., Coll., vol. 5, pp. 1064–1066, "2-(p-Tolylsulfonyl)Dihydroisoindole", J. Bornstein et al.
Chem. Ber., vol. 51, pp. 100–108, "J. v. Braun und Z. Kohler: Oxybasen und Homologe Choline, II²)", Aus Dem Chem Institut der Univ und Techn . . .

Primary Examiner—Mary E. Ceperley
Attorney, Agent, or Firm—Oblon, Spivak, McClelland, Maier & Neustadt

[57] ABSTRACT

A process for producing a compound of the formula:

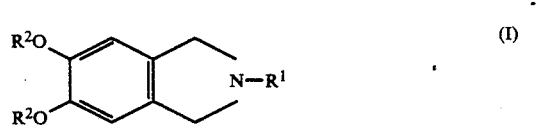

(I)

wherein $R^1$ is a hydrogen atom, a lower alkyl group or an aralkyl group, and $R^2$ is a hydrogen atom or a hydroxyl-protecting group, or a salt thereof, which comprises removing from a compound of the formula:

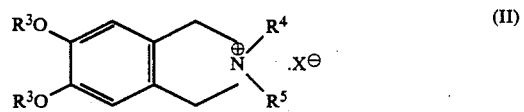

(II)

wherein $R^3$ is a hydrogen atom or a hydroxyl-protecting group, $R^4$ and $R^5$ which may be the same or different are N-protecting groups selected from the group consisting of lower alkyl groups and aralkyl groups, and $X^\ominus$ is an anion, the N-protecting group(s), if necessary, together with the hydroxyl-protecting group.

9 Claims, No Drawings

PROCESS FOR THE PRODUCTION OF ISOINDOLINE DERIVATIVES, NOVEL INTERMEDIATES AND PROCESS FOR THEIR PRODUCTION

The present invention relates to a novel process for producing 5,6-disubstituted isoindoline derivatives, novel isoindolinium derivatives useful as intermediates for the 5,6-disubstituted isoindoline derivatives and processes for the production of such intermediates Heretofore, the following processes have been known for the production of isoindoline derivatives:

(1) Process disclosed in Org. Synth., Coll. Vol. 5, p. 406 and p. 1064:

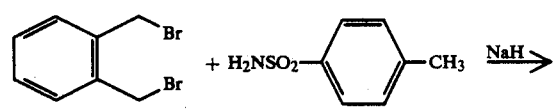

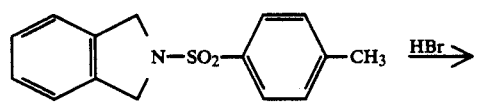

(2) Process disclosed in Chem. Ber., Vol. 51, p. 103 (1918):

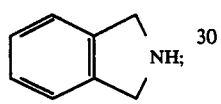

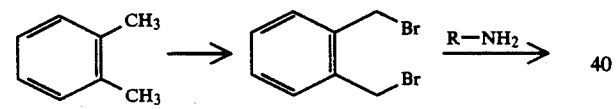

(3) Process disclosed in J. Pharm. Sci., Vol. 53, p. 981

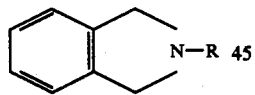

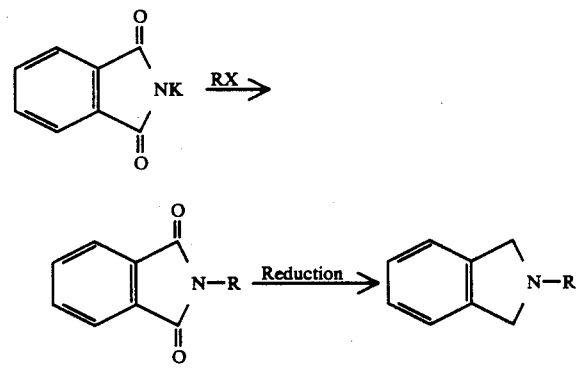

(4) Process disclosed in J. Org. Chem., Vol. 19, p. 884 (1954), and ibid. Vol. 40, p. 957 (1975):

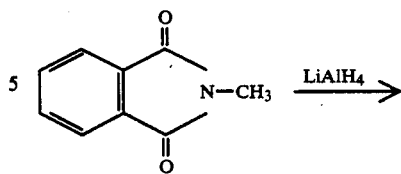

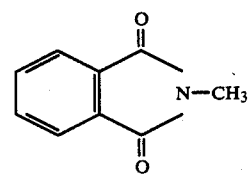

(5) Process disclosed in J. Am. Chem. Soc., Vol. 77, p. 616 (1953) and ibid. Vol. 79, p. 3167 (1957):

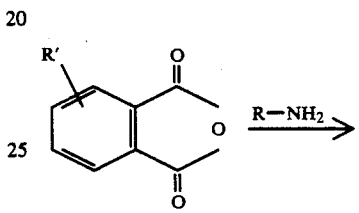

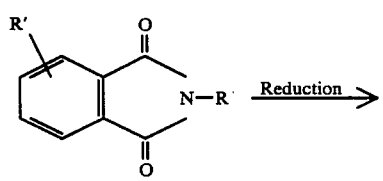

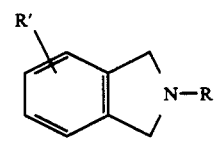

However, the above processes are restricted to a case where the benzene ring of the isoindoline nucleus has no substituent or a case where the benzene ring of the isoindoline nucleus has only one substituent. None of the processes is suitable for mass production, since the yield is low in each of the processes.

The compound according to the second aspect of the present invention i.e. an N,N-disubstituted isoindolinium salt which is on its 5- and 6-positions substituted by hydroxyl groups or protected hydroxyl groups, is a novel compound not disclosed in any literatures.

Processes for the production of N,N-disubstituted isoindolinium derivatives wherein the benzene nucleus is unsubstituted or mono-substituted, are disclosed in Chem. Abstr., Vol. 74, 53389 (1971) and in J. Chem. Soc., Vol. 77, p. 616 (1953) and ibid. Vol. 79, p. 3167 (1957).

Namely, Chem. Abstr., Vol. 74, 53389 (1971) discloses a process for preparing a quaternary isoindolinium salt by reacting a quaternary ammonium salt starting material with a base as shown by the following Scheme:

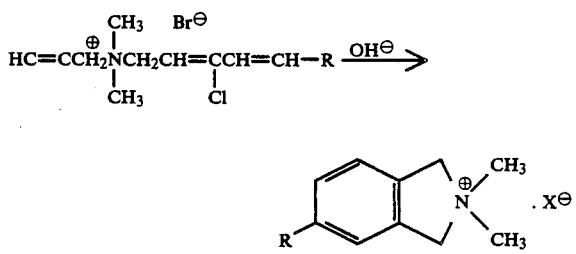

However, the preparation of the quaternary ammonium salt starting material is complicated and involves many steps, and the process is not industrially advantageous.

On the other hand, J. Am. Chem. Soc., Vol. 77, p. 616 (1953) and ibid. Vol. 79, p. 3167 (1957) disclose a general process for the production of a quaternary isoindolinium salt as shown by the following Scheme:

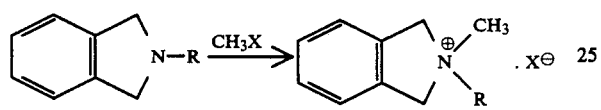

However, as mentioned above, the conventional processes for the production of the N-substituted isoindoline starting material are not suitable for mass production since the yield is low in each process. Further, it is usually difficult to introduce hydroxyl groups or protected hydroxyl groups directly to the 5- and 6-positions of the isoindoline nucleus. Further, the preparation of such a compound involves many steps and the yield is expected to be low. As such, the process is not industrially advantageous.

The present inventors have conducted extensive research with an aim to develop a process for the production of 5,6-disubstituted isoindoline derivatives and, as a result, have found a process for producing a 5,6-disubstituted isoindoline derivative of the formula I in good yield.

The present invention provides a process for producing a compound of the formula:

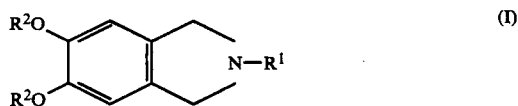

wherein $R^1$ is a hydrogen atom, a lower alkyl group or an aralkyl group, and $R^2$ is a hydrogen atom or a hydroxyl-protecting group, or a salt thereof, which comprises removing from a compound of the formula:

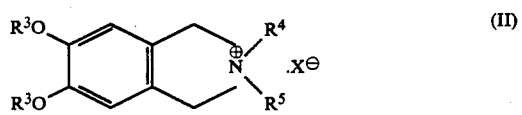

wherein $R^3$ is a hydrogen atom or a hydroxyl-protecting group, $R^4$ and $R^5$ which may be the same or different are N-protecting groups selected from the group consisting of lower alkyl groups and aralkyl groups, and $X^\ominus$ is an anion, the N-protecting group(s) and, if necessary, the hydroxyl-protecting group.

The compound of the formula II used as the starting material in the above process is a novel compound and can be prepared by (1) reacting a compound of the formula:

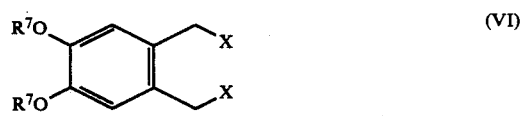

wherein $R^7$ is a hydrogen atom or a hydroxyl-protecting group, and X is a halogen atom, with a secondary amine of the formula:

wherein $R^4$ and $R^5$ are as defined above, in the presence of an acid binding agent and, if necessary, removing the hydroxyl-protecting group, or (2) reacting a compound of the formula:

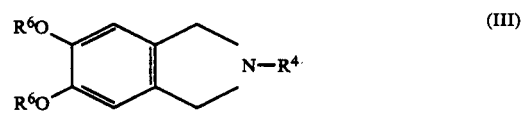

wherein $R^4$ is a lower alkyl group or an aralkyl group, and $R^6$ is a hydrogen atom or a hydroxyl-protecting group, with a lower alkylating or aralkylating agent and, if necessary, removing the hydroxyl-protecting group.

The compound of the formula III can be prepared by reacting a compound of the formula:

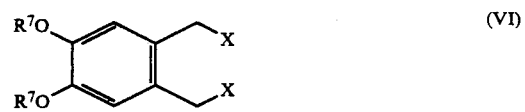

wherein $R^7$ and X are as defined above with a primary amine of the formula:

wherein $R^4$ is as defined above, and, if necessary, removing the hydroxyl-protecting group.

The above processes of the present invention may be summarized as follows:

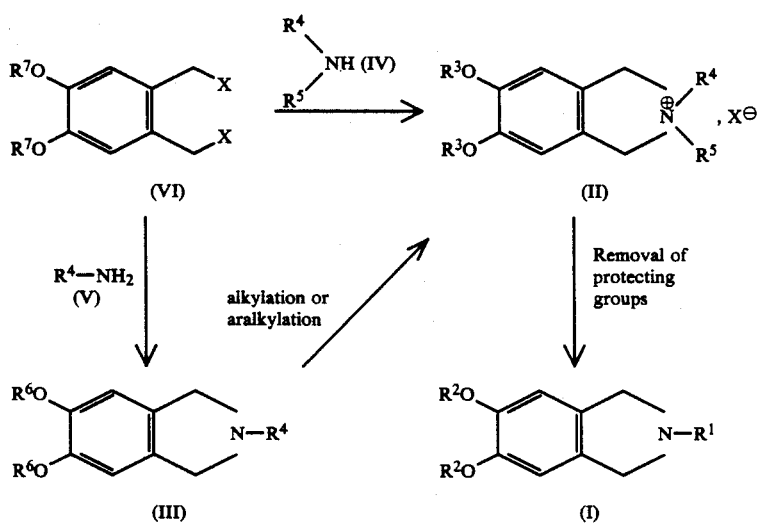

Now, the present invention will be described in detail with reference to the preferred embodiments.

Firstly, the terms used in this specification will be defined.

The lower alkyl group means a straight chain or branched alkyl group having from 1 to 4 carbon atoms, such as a methyl group, an ethyl group, a propyl group, an isopropyl group, a butyl group, an isobutyl group, a sec-butyl group or a tert-butyl group. Particularly preferred are a methyl group, an ethyl group and a propyl group.

The aralkyl group means an aralkyl group having from 7 to 12 carbon atoms, such as a benzyl group, a 3-methoxybenzyl group, a 4-methoxybenzyl group, a 3,4-dimethoxybenzyl group, an α-methylbenzyl group, a phenethyl group, a 3-phenylpropyl group, a 1-naphthylmethyl group or a diphenylmethyl group. Particularly preferred are a benzyl group, an α-methylbenzyl group and a 4-methoxybenzyl group.

The halogen atom means a halogen atom such as a chlorine atom, a bromine atom or an iodine atom. Particularly preferred is a chlorine atom.

The anion includes, for example, a halide ion such as a chloride ion, a bromide ion or an iodide ion, a sulfate ion, a hydrogen sulfate ion, a methylsulfate ion, a p-toluenesulfonate ion, a methanesulfonate ion and a trifluoroacetate ion.

The hydroxyl-protecting group may be, for example, an acetyl group, a methyl group, a benzyl group or an ethoxycarbonyl group which can readily be removed by an acid, a base, chemical reduction or catalytic reduction, or a cyclic acetal such as methylene acetal, ethylene acetal or benzylidene acetal, an orthoester such as methoxymethylidene or methoxyethylidene, a cyclic ketal such as isopropylidene ketal, or a cyclic carbonate, which is formed by the combination of two protecting groups.

The N-protecting group may be a lower alkyl group such as a methyl group, an ethyl group, a propyl group, an isopropyl group, a butyl group, an isobutyl group, a sec-butyl group or a tert-butyl group, or an aralkyl group such as a benzyl group, a 3-methoxybenzyl group, a 4-methoxybenzyl group, a 3,4-dimethoxybenzyl group, a diphenylmethyl group, an α-methylbenzyl group, a phenethyl group, a 3-phenylpropyl group or a 1-naphthylmethyl group.

The salt of the compound of the formula I may be a salt of an inorganic acid such as a hydrochloride, a nitrate, a hydrobromide, a sulfate or a perchlorate, a sulfonate such as a p-toluenesulfonate or a methanesulfonate, or a salt of an organic acid such as a formate or an acetate.

Among the compounds of the formula I of the present invention, preferred are as folllows:

1. 5,6-dihydroxyisoindoline.
2. 5,6-dimethoxyisoindoline
3. 5,6-diacetoxyisoindoline
4. 5,6-dihydroxy-N-methylisoindoline
5. 5,6-dimethoxy-N-methylisoindoline
6. 5,6-diacetoxy-N-methylisoindoline
7. N-benzyl-5,6-dihydroxyisoindoline
8. N-benzyl-5,6-dimethoxyisoindoline
9. 5,6-diacetoxy-N-benzylisoindoline
10. N-ethyl-5,6-dimethoxyisoindoline
11. N ethyl-5,6-dihydroxyisoindoline
12. 5,6-dimethoxy-N-propylisoindoline
13. 5,6-dihydroxy-N-propylisoindoline
14. 5,6-dimethoxy-N-isopropylisoindoline
15. 5,6-dihydroxy-N-isopropylisoindoline
16. N-butyl-5,6-dimethoxyisoindoline
17. N-butyl-5,6-dihydroxyisoindoline
18. N-isobutyl-5,6-dimethoxyisoindoline
19. N-isobutyl-5,6-dihydroxyisoindoline
20. N-sec-butyl-5,6-dimethoxyisoindoline
21. N-sec-butyl-5,6-dihydroxyisoindoline
22. N-tert-butyl-5,6-dimethoxyisoindoline
23. N-tert-butyl-5,6-dihydroxyisoindoline
24. 5,6-dimethoxy-N-(4-methoxybenzyl)isoindoline
25. 5,6-dihydroxy-N-(4-methoxybenzyl)isoindoline
26. 5,6-dimethoxy-N-phenethylisoindoline
27. 5,6-dihydroxy-N-phenethylisoindoline
28. 5,6-dimethoxy-N-(3-phenylpropyl)isoindoline
29. 5,6-dihydroxy-N-(3-phenylpropyl)isoindoline
30. 5,6-dimethoxy-N-(1-naphthylmethyl)isoindoline
31. 5,6-dihydroxy-N-(1-naphthylmethyl)isoindoline The compounds of the present invention are represented by the formula:

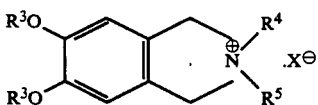

(II)

wherein $R^3$ is a hydrogen atom or a hydroxyl-protecting group, $R^4$ and $R^5$ which may be the same or different are N-protecting group(s) selected from the group consisting of lower alkyl groups and aralkyl groups, and $X^\ominus$ is an anion.

Among the compounds of the formula II of the present invention, preferred are those represented by the formula:

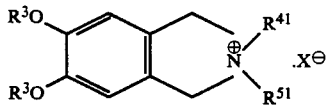

(II-a)

wherein $R^3$ and $X^\ominus$ are as defined above, and $R^{41}$ and $R^{51}$ which may be the same or different are N-protecting group(s) selected from the group consisting of $C_{1-4}$ alkyl groups and $C_{7-12}$ aralkyl groups. The compounds of the formula II-a include the compounds represented by the following formulas II-b, II-c and II-d:

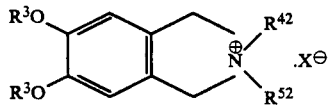

(II-b)

wherein $R^3$ and $X^\ominus$ are as defined above, and $R^{42}$ and $R^{52}$ which may be the same or different are $C_{1-4}$ alkyl groups.

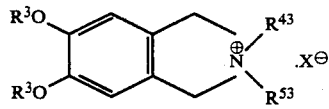

(II-c)

wherein $R^3$ and $X^\ominus$ are as defined above and $R^{43}$ and $R^{53}$ which may be the same or different are $C_{7-12}$ aralkyl groups.

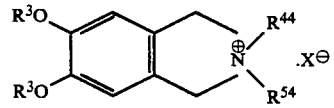

(II-d)

wherein $R^3$ and $X^\ominus$ are as defined above, $R^{44}$ is a $C_{1-4}$ alkyl group, and $R^{54}$ is a $C_{7-12}$ aralkyl group.

Among the compounds of the formula II of the present invention, preferred are as follows:
1. N-benzyl-5,6-dimethoxy-N-methylisoindolinium chloride
2. N-benzyl-5,6-dimethoxy-N-methylisoindolinium bromide
3. N-benzyl-5,6-dimethoxy-N-methylisoindolinium iodide
4. N-benzyl-5,6-dimethoxy-N-methylisoindolinium hydrogen sulfate
5. N-benzyl-5,6-dimethoxy-N-methylisoindolinium sulfate
6. N-benzyl-5,6-dihydroxy-N-methylisoindolinium methylsulfate
7. N-benzyl-5,6-dihydroxy-N-methylisoindolinium chloride
8. N-benzyl-5,6-dihydroxy-N-methylisoindolinium bromide
9. N-benzyl-5,6-dihydroxy-N-methylisoindolinium iodide
10. N-benzyl-5,6-dihydroxy-N-methylisoindolinium hydrogen sulfate
11. N-benzyl-5,6-dihydroxy-N-methylisoindolinium sulfate
12. N-benzyl-5,6-dihydroxy-N-methylisoindolinium methylsulfate Among the isoindolinium ions of the compounds of the formula II, preferred are as folllows:
1. N,N-dibenzyl-5,6-dimethoxyisoindolinium ion
2. N,N-dibenzyl-5,6-dihydroxyisoindolinium ion
3. 5,6-diacetoxy-N,N-dibenzylisoindolinium ion
4. 5,6-dimethoxy-N,N-dimethylisoindolinium ion
5. 5,6-dihydroxy-N,N-dimethylisoindolinium ion
6. 5,6-diacetoxy-N,N-dimethylisoindolinium ion
7. N-benzyl-5,6-dimethoxy-N-methylisoindolinium ion
8. N-benzyl-5,6-dihydroxy-N-methylisoindolinium ion
9. 5,6-diacetoxy-N-benzyl-N-methylisoindolinium ion
10. 5,6-dimethoxy-N-(4-methoxybenzyl)-N-methylisoindolinium ion
11. 5,6-dimethoxy-N-(3,4-dimethoxybenzyl)-N-methyl-isoindolinium ion
12. 5,6-dimethoxy-N-methyl-N-(α-methylbenzyl)-isoindolinium ion
13. 5,6-dimethoxy-N-methyl-N-diphenylmethylisoindolinium ion
14. N-benzyl-N-ethyl-5,6-dimethoxyisoindolinium ion
15. N-benzyl-N-ethyl-5,6-dihydroxyisoindolinium ion
16. N-benzyl-5,6-dimethoxy-N-propylisoindolinium ion
17. N-benzyl-5,6-dihydroxy-N-propylisoindolinium ion
18. N-benzyl-5,6-dimethoxy-N-isopropylisoindolinium ion
19. N-benzyl-5,6-dihydroxy-N-isopropylisoindolinium ion
20. N-benzyl-N-butyl-5,6-dimethoxyisoindolinium ion
21. N-benzyl-N-butyl-5,6-dihydroxyisoindolinium ion
22. N-benzyl-N-isobutyl-5,6-dimethoxyisoindolinium ion
23. N-benzyl-N-isobutyl-5,6-dihydroxyisoindolinium ion
24. N-benzyl-N-sec-butyl-5,6-dimethoxyisoindolinium ion
25. N-benzyl-N-sec-butyl-5,6-dihydroxyisoindolinium ion
26. N-benzyl-N-tert-butyl-5,6-dimethoxyisoindolinium ion
27. N-benzyl-N-tert-butyl-5,6-dihydroxyisoindolinium ion
28. N-benzyl-5,6 dimethoxy-N-phenethylisoindolinium ion
29. N-benzyl-5,6-dihydroxy-N-phenethylisoindolinium ion
30. N-benzyl-5,6-dimethoxy-N-(3-phenylpropyl)isoindolinium ion 31. N-benzyl-5,6-dihydroxy-N-(3-phenylpropyl-)isoindolinium ion Among the listed compounds, particularly preferred are compounds of 1, 2, 4, 5, 7, 8, 9, 10, 14, 16, 18, 20, 22, 24, 26, 28 and 30. Most preferred are the compounds of 1, 4, 7, 8, 9, 14, 16 and 18. The above-mentioned isoindolinium ions form salts together with anions such as a halide ion, a sulfate ion, a hydogen sulfate ion, a methylsulfate ion, a p-toluenesulfate ion, a methanesulfate ion and a trifluoroacetate ion.

Now, the processes for the production of the compound of the formula I and the compound of the formula II will be described.

Firstly, the processes for the production of the compound of the formula I will be described.

The compound of the formula I can be prepared from the compound of the formula II by one of the following processes A, B, C and D.

PROCESS A

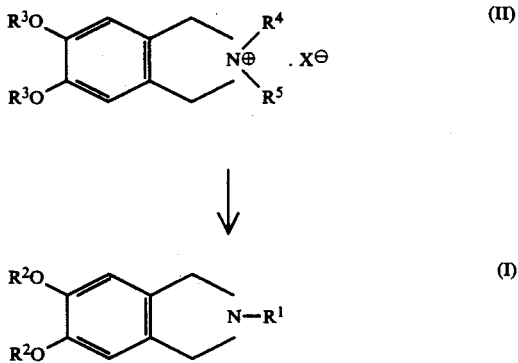

This process comprises removing the N-protecting group(s), if necessary, together with the hydroxyl-protecting group, from the compound of the formula II to obtain the compound of the formula I.

The removal of the protecting groups will be described.

The removal of the protecting groups can be conducted in accordance with the methods disclosed in e.g. "Protective Groups in Organic Synthesis" edited by T. W. Green and published in 1981 by Wiley and "Protective Groups in Organic Chemistry" edited by J. F. W. McOmie and published in 1973 by Plenum Press. For example, preferred methods include a reaction with a halotrimethylsilane such as iodotrimethylsilane with a nucleophilic reagent such as ethyl mercaptan, thiophenol, sodium sulfide or sodium cyanide, with a Lewis acid such as aluminum chloride, aluminum chloride-ethyl mercaptan, boron trifluoride, boron tribromide, boron trichloride, hydroiodic acid or hydrobromic acid or with an amine salt such as pyridine hydrochloride, pyridine hydrobromide or pyridine hydriodide; decomposition by means of a base such as sodium hydroxide, potassium hydroxide, sodium carbonate or potassium carbonate, or by means of an acid such as hydrochloric acid, hydrobromic acid, hydriodic acid or sulfuric acid; and protective group-removal by reduction or heating.

The following four methods may be mentioned as particularly preferred methods.

Removal of the Protecting Groups by an Acid

The protecting groups of the compound of the formula II can be removed by heating the compound of the formula II together with an acid of a proper concentration in an amount of from 1 to 20 times, preferably from 3 to 10 times the amount of the compound. As such an acid, an inorganic acid such as hydrochloric acid, hydrobromic acid, hydroiodic acid or sulfuric acid may be mentioned.

The reaction may be facilitated by an addition of acetic acid, propionic acid or phenol in a proper amount to the reaction solution. The reaction may be completed by heating at a temperature of from 70° to 130° C. for from 2 to 30 hours.

Removal of the Protecting Groups by Chemical Reduction

The protective groups of the compound of the formula II can be removed by reacting the compound of the formula II with an acid in an amount of from 1 to 20 times, preferably from 3 to 10 times, the amount of the compound in the presence of a reducing agent in an amount of from 1 to 30 times by weight, preferably from 3 to 20 times by weight, the amount of the compound.

Suitable reducing agents include a metal such as iron, zinc or tin and a metal compound such as chromium acetate or chromium chloride.

Suitable acids include an organic acid such as formic acid, acetic acid, trifluoroacetic acid or propionic acid and an inorganic acid such as hydrochloric acid, hydrobromic acid or sulfuric acid.

The reaction is usually conducted in a solvent such as water, methanol, ethanol, propanol, diethyl ether, tetrahydrofuran or dioxane, or in a solvent mixture thereof. Further, the above-mentioned acids may be used as solvents.

There is no particular restriction as to the reaction temperature, and the reaction may be conducted under cooling or under heating. The reaction is preferably conducted from room temperature to 100° C.

Removal of the Protecting Groups by Catalytic Reduction

The protective groups ca be removed by dissolving the compound of the formula II in a solvent such as water, methanol, ethanol, propanol, isopropanol, acetic acid, hydrochloric acid, hydrobromic acid or sulfuric acid or in a solvent mixture thereof, and then catalytically reducing it at a temperature of from 20° to 80° C. for from 2 to 10 hours by means of a catalyst in an amount of from 5 to 20% by weight, preferably from 5 to 10% by weight, relative to the compound of the formula II.

Suitable catalysts useful for the catalytic reduction include a palladium catalyst such as palladium carbon, palladium oxide, palladium black, colloidal palladium, palladium sponge, palladium-barium carbonate or palladium-barium sulfate; a platinum catalyst such as a platinum plate, platinum sponge, platinum black, platinum wire or platinum chloride; a nickel catalyst such as nickel oxide, reduced nickel or Raney nickel; a cobalt catalyst such as reduced cobalt or Raney cobalt; an iron catalyst such as reduced iron or Raney iron; and a copper catalyst such as reduced copper, Raney copper or Ullmann copper.

Removal of the Protecting Groups by Heating or by Means of a Base

The protecting groups of the compound of the formula II can be removed by heating the compound in the presence or absence of a solvent or by heating the compound together with an inorganic base in a catalytically effective amount or in an excess amount, preferably from 3 to 20 times in excess.

Such an inorganic base may be an alkali metal hydroxide such as sodium hydroxide or potassium hydroxide; an alkali metal carbonate such as sodium carbonate or potassium carbonate; an alkali metal hydrogencarbonate such as sodium hydrogen carbonate or potassium hydrogen carbonate; an alkaline earth metal oxide such as magnesium oxide; or an alkali metal alkoxide such as sodium methoxide, sodium ethoxide or potassium tert-butoxide.

The reaction is usually conducted in a solvent such as water, methanol, ethanol, benzene, toluene, xylene, diphenyl ether or Dowtherm A ®, or an organic base solvent such as trimethylamine, triethylamine, pyridine, picoline, N,N-dimethylaniline, quinoline or isoquinoline, or in a solvent mixture thereof, or in the absence of a solvent, by heating at a temperature of from 80° to 300° C. for from 2 to 50 hours.

By properly selecting the types of the protecting groups or the methods and reaction conditions for the removal of the protecting groups, it is possible to simultaneously remove the N-protecting groups and the hydroxyl-protecting groups. Otherwise, it is possible to selectively remove either the N-protecting groups or the hydroxyl-protecting groups. There is no particular restriction a to the order for the removal of the protecting groups.

After the completion of the reaction, the compound of the formula I or its salt can be isolated from the reaction solution and purified by conventional separating means such as solvent extraction, recrystallization or chromatography. The compound of the formula I can be converted to a salt of an inorganic acid such as a hydrochloride, hydrobromide, sulfate, nitrate or perchlorate, or to an organic-sulfonate such as a methanesulfonate or p-toluenesulfonate.

PROCESS B

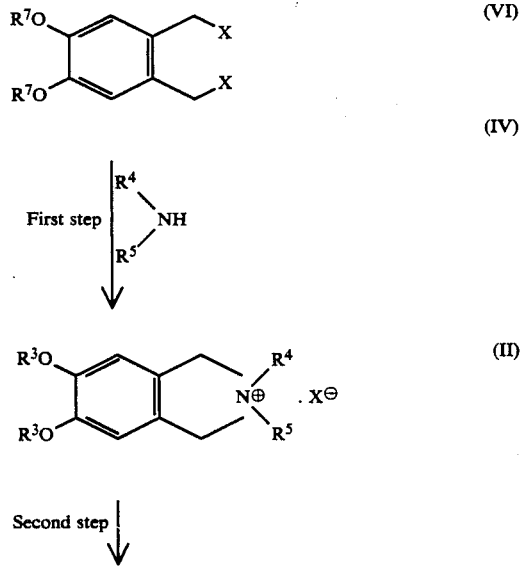

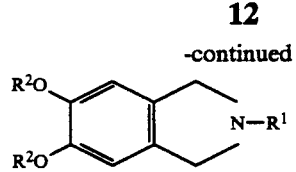

This process comprises reacting a 4,5-bis(halomethyl)catechol derivative of the formula VI with a secondary amine of the formula IV in the presence of an acid binding agent and, if necessary, removing the hydroxyl-protecting groups, to obtain a compound of the formula II, and then removing from the compound of the formula II the N-protecting group(s), if necessary, together with the hydroxyl groups, to obtain the compound of the formula I.

The reaction of the 4,5-bis(halomethyl)catechol derivative of the formula VI with the secondary amine of the formula IV is usually conducted in an inert organic solvent such as acetone, acetonitrile, tetrahydrofuran, dioxane, ethyl acetate, butyl acetate, benzene, toluene, xylene, methylene chloride, chloroform, N,N-dimethylformamide or dimethylsulfoxide, or in a two phase system of such an inert organic solvent and water, in the presence of an acid binding agent, by using the secondary amine of the formula IV or its salt in an amount of from 1.0 to 1.5 equivalent, preferably from 1.1 to 1.2 equivalent, relative to the 4,5-bis(halomethyl)catechol derivative of the formula VI. The acid binding agent is usually used in an amount of from 1.0 to 2.0 equivalent, preferably from 1.1 to 1.5 equivalent. The reaction is usually conducted at a temperature of from 0° to 100° C., preferably from 20° to 70° C. and can be completed usually in from 2 to 40 hours.

When the reaction is conducted in a two phase system, a phase transfer catalyst as disclosed in e.g. "Phase Transfer Catalysis in Organic Synthesis" 1977, W. P. Weber and G. W. Gokel, may be employed. Such a phase transfer catalyst may be, for example, tetramethylammonium chloride, benzyltrimethylammonium chloride, benzyltriethylammonium chloride, benzyltributylammonium chloride, tetrabutylammonium bromide, tetrabutylammonium hydrogen sulfate or trioctylmethylammonium chloride.

The acid binding agent useful for this reaction includes an alkali metal hydroxide such as sodium hydroxide or potassium hydroxide, an alkali metal carbonate such as sodium carbonate or potassium carbonate, an alkali metal hydrogen carbonate such as sodium hydrogen carbonate or potassium hydrogen carbonate, an alkaline earth metal oxide such as magnesium oxide, an alkali metal alkoxide such as sodium methoxide, sodium ethoxide or potassium tert-butoxide, a tertiary amine such as trimethylamine, triethylamine, N,N-diisopropylethylamine, N-methylmorpholine or N,N-dimethylaniline, a pyridine compound such as pyridine, picoline or lutidine, and an organic amine such as quinoline or isoquinoline.

The secondary amine of the formula IV includes, for example, dimethylamine, N-methylethylamine, N-methylpropylamine, N-methylisopropylamine, N-methylbutylamine, N-methylisobutylamine, N-methyl-sec-butylamine, N-methyl-tert-butylamine, N-methylbenzylamine, N-methyl(α-methylbenzyl)amine, N-methyl(3-methoxybenzyl)amine, N-methyl(4-methoxybenzyl)amine, N-methyl(3,4-dimethoxybenzyl)amine, N-methyldiphenylmethylamine, N-methylphenethylamine, N-methyl(3-phenylpropyl)amine, N-methyl(1- naphthylmethyl)amine, diethylamine, N-ethylpropylamine, N-ethylisopropylamine, N-ethylbutylamine, N-ethylisobutylamine, N-ethyl-sec-butylamine, N-ethyl-tert-butylamine, N-ethylbenzylamine, N-ethyl(α-methylbenzyl)amine, N-ethyl(3-methoxybenzyl)amine, N-ethyl(4-methoxybenzyl)amine, N-ethyl(3,4-dimethoxybenzyl)amine, N-ethyldiphenylmethylamine, N-ethylphenethylamine, N-ethyl(3-phenylpropyl)amine, N-ethyl(1-naphthylmethyl)amine, dipropylamine, N-propylisopropylamine, N-propylbutylamine, N-propylisobutylamine, N-propyl-sec-butylamine, N-propyl-tert-butylamine, N-propylbenzylamine, N-propyl-(α-methylbenzyl)amine, N-propyl(3-methoxybenzyl)amine, N-propyl(4-methoxybenzyl)amine N-propyl(3,4-dimethoxybenzyl)amine, N-propyldiphenylmethylamine, N-propylphenethylamine, N-propyl(3-phenylpropyl)amine, N-propyl(1-naphthylmethyl)amine, diisopropylamine, N-isopropylbutylamine, N-isopropylisobutylamine, N-isopropyl-sec-butylamine, N-isopropyl-tert-butylamine, N-isopropylbenzylamine, N-isopropyl(α-methybenzyl)amine, N-isopropyl(3-methoxybenzyl)amine, N-isopropyl(4-methoxybenzyl)amine, N-isopropyl(3,4-dimethoxybenzyl)amine, N-isopropyldiphenylmethylamine, N-isopropylphenethylamine, N-isopropyl(3-phenylpropyl)amine, N-isopropyl(1-naphthylmethyl)amine, dibutylamine, N-butylisobutylamine, N-butyl-sec-butylamine, N-butyl-tert-butylamine, N-butylbenzylamine, N-butyl(α-methylbenzyl)amine, N-butyl(3-methoxybenzyl)amine, N-butyl(4-methoxybenzyl)amine, N-butyl(3,4-dimethoxybenzyl)amine, N-butyldiphenylmethylamine, N-butylphenethylamine, N-butyl(1-naphthylmethyl)amine, diisobutylamine, dibenzylamine, bis(3-methoxybenzyl)amine, bis(4-methoxybenzyl)amine, bis(3,4-dimethoxybenzyl)amine and N-tert-butylbenzylamine. Particularly preferred are N-substituted benzylamines such as N-methylbenzylamine, N-ethylbenzylamine, N-propylbenzylamine and dibenzylamine.

The salt of the secondary amine of the formula IV may be, for example, a hydrochloride, a hydrobromide, a sulfate or an acetate.

In this process, the removal of the hydroxyl-protecting group may be conducted in the same manner as in the process A.

PROCESS C

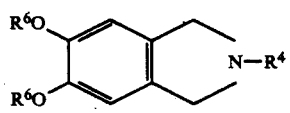
(III)

First step | Lower alkylating or aralkylating agent

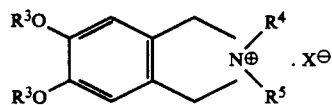
(II)

Second step 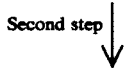

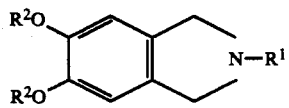
(I)

This process comprises reacting a compound of the formula III with a lower alkylating or aralkylating agent and, if necessary, removing the hydroxyl-protecting group, to obtain a compound of the formula II, and then removing from the compound of the formula II the N-protecting group(s), if necessary, together with the hydroxyl-protecting group, to obtain the compound of the formula I.

First Step

This step comprises reacting the N-substituted 5,6-disubstituted isoindoline derivative of the formula III with a lower alkylating or aralkylating agent and, if necessary, removing the hydroxyl-protecting groups, to obtain the N,N-disubstituted 5,6-disubstituted isoindolinium derivative of the formula II.

The N-lower alkylation or N-aralkylation of the N-substituted 5,6-disubstituted isoindoline derivative of the formula III is usually conducted in an organic solvent such as methylene chloride, chloroform, ethyl ether, ethyl acetate, tetrahydrofuran, acetonitrile, acetone, methanol, ethanol, N,N-dimethylformamide or dimethylsulfoxide, or in a solvent mixture thereof, by using a lower alkylating or aralkylating agent in an amount of from 1 to 30 equivalent, preferably from 1 to 1.5 equivalent, relative to the isoindoline derivative of the formula III.

Instead of the above organic solvent, an excess amount of the lower alkylating or aralkylating agent may be employed.

The reaction is conducted usually at a temperature of from 0° to 70° C. and can be completed in from 0.5 to 30 hours.

The lower alkylating or aralkylating agent is meant for a reagent which is readily available or can readily be prepared. Such an alkylating or aralkylating agent includes a lower alkylhalide or an aralkylhalide composed of chloride, bromide or iodide, or a lower alkylhalide or an alkyl ester of trifluoromethane acetic acid, methanesulfonic acid, p-toluenesulfonic acid or sulfuric acid.

The lower alkyl group of such a reagent includes, for example, a methyl group, an ethyl group, a propyl group, an isopropyl group, a butyl group, an isobutyl group, a sec-butyl group or a tert-butyl group. Particularly preferred are a methyl group, an ethyl group and a propyl group.

The aralkyl group of such a reagent includes, for example, a benzyl group, an α-methylbenzyl group, a 3-methoxybenzyl group, a 4-methoxybenzyl group, a 3,4-dimethoxybenzyl group, a diphenylmethyl group, a phenethyl group, a 3-phenylpropyl group and 1-naphthylmethyl group. Particularly preferred are a benzyl group, an α-methylbenzyl group and a 4-methoxybenzyl group.

Second Step

This step comprises removing the N-protecting group(s) and, if necessary, the hydroxyl-protecting groups from the N,N-disubstituted 5,6-disubstituted isoindolinium derivative of the formula II, to obtain the comound of the formula I.

This step can be conducted in the same manner as the step of preparing the compound of the formula I from the compound of the formula II in the process A. In this process, the compound of the formula II may be isolated or may not be isolated before subjecting it to the subsequent reaction.

The starting material of the present step i.e. the compound of the formula III can be readily prepared, for example, by using a 4,5-bis(halomethyl)catechol derivative of the formula VI and a usual primary amine of the formula V as will be described hereinafter.

PROCESS D

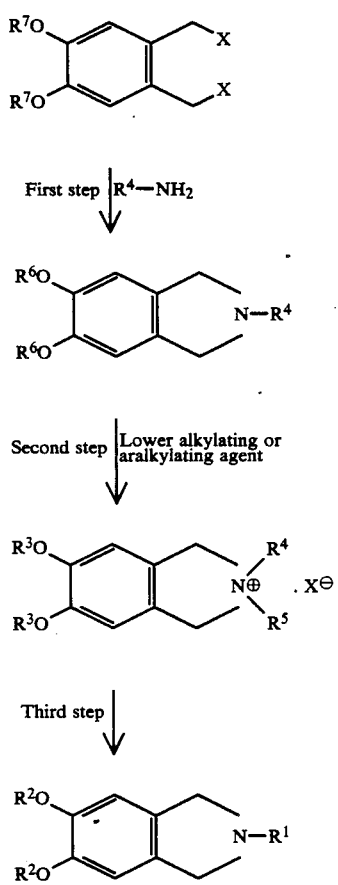

This process comprises a first step of reacting a 4,5-bis(halomethyl)catechol derivative of the formula VI with a primary amine of the formula V in the presence of an acid binding agent and, if necessary, removing the hydroxyl-protecting groups, to obtain a compound of the formula III, a second step of reacting this compound of the formula III with a lower alkylating or aralkylating agent and, if necessary, removing the hydroxyl-protecting groups, to obtain a compound of the formula II, and a third step of removing from the compound of the formula II the N-protecting group(s), if necessary, together with the hydroxyl-protecting group, to obtain the compound of the formula I.

First Step

This step comprises reacting the 4,5-bis(halomethyl)-catechol derivative of the formula VI with the primary amine of the formula V or its salt in the presence of an acid binding agent and, if necessary, removing the hydroxyl-protecting groups, to obtain the N-substituted 5,6-disubstituted isoindoline derivative of the formula III.

The reaction of the 4,5-bis(halomethyl)catechol derivative of the formula VI with the primary amine of the formula V is conducted in the same manner as the step of preparing the compound of the formula II from the compound of the formula VI in the process B. However, the acid binding agent is used in an amount of from 2 to 10 equivalent.

The primary amine of the formula V includes a lower alkylamine such as methylamine, ethylamine, propylamine, isopropylamine, butylamine, isobutylamine, sec-butylamine or tert-butylamine, and an aralkyl amine such as benzylamine, 3-methoxybenzylamine, 4-methoxybenzylamine, 3,4-dimethoxybenzylamine, diphenylmethylamine, α-methylbenzylamine, phenethylamine, 3-phenylpropylamine or 1-naphthylmethylamine. Particularly preferred are methylamine, ethylamine, benzylamine, 4-methoxybenzylamine and phenethylamine.

As the salt of the primary amine, a hydrochloride, a hydrobromide, a sulfate, a nitrate or an acetate may be mentioned.

Second Step

This step comprises reacting the N-substituted 5,6-disubstituted isoindoline derivative of the formula III with a lower alkylating or aralkylating agent and if necessary, removing the hydroxyl-protecting groups, to obtain the N,N-disubstituted 5,6-disubstituted isoindolinium derivative of the formula II.

This step can be conduted in the same manner as the step of preparing the compound of the formula II from the compound of the formula III in the process C.

Third Step

This step can be conducted in the same manner as the step of preparing the compound of the formula I from the compound of the formula II in the process A.

In this process, the compound of the formula II and the compound of the formula III may be isolated or may not be isolated before subjecting it to the respective subsequent reactions.

The 4,5-bis(halomethyl)catechol derivative of the formula VI used as the starting compound can be prepared by the method disclosed in J. Am. Chem. Soc., Vol. 72, p. 2989 (1952).

Now, the processes for the production of the novel N,N-disubstituted 5,6-disubstituted isoindolinium derivative of the formula II of the present invention will be described.

The compound of the formula II can be prepared by one of the following processes E, F and G.

PROCESS E

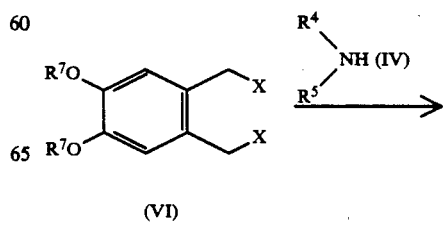

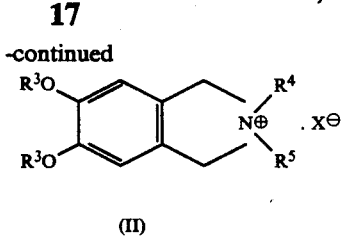

(II)

This process comprises reacting a 4,5-bis(halomethyl)catechol derivative of the formula VI with a secondary amine of the formula IV in the presence of an acid binding agent and, if necessary, removing the hydroxyl-protecting groups, to obtain a compound of the formula II. This process can be conducted in the same manner as the first step of the process B.

PROCESS F

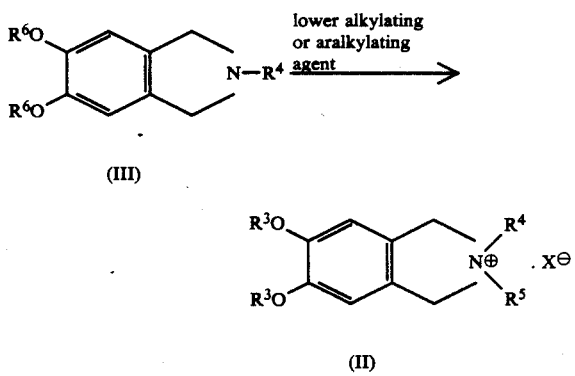

This process comprises reacting an N-substituted 5,6-disubstituted isoindoline derivative of the formula III with a lower alkylating or aralkylating agent and, if necessary, removing the hydroxyl-protecting groups, to obtain a compound of the formula II. The process can be conducted in the same manner as the first step of the process C to obtain the desired compound of the formula II.

PROCESS G

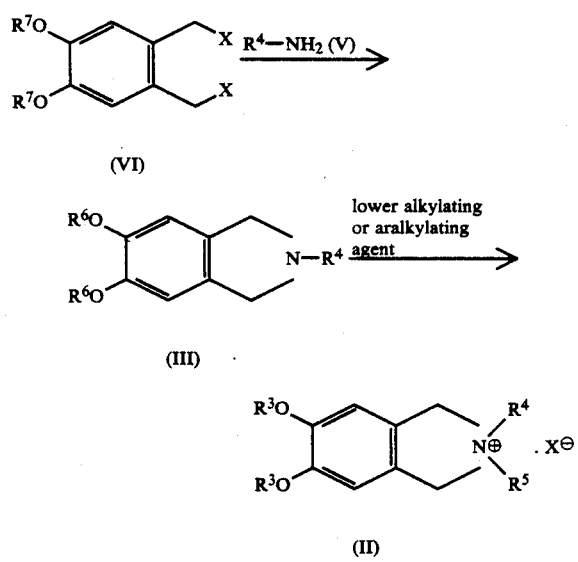

This process comprises reacting a 4,5-bis(halomethyl)catechol derivative of the formula VI with a primary amine of the formula V in the presence of an acid binding agent and, if necessary, removing the hydroxyl-protecting groups, to obtain a compound of the formula III, and then reacting the compound of the formula III with a lower alkylating or aralkylating agent and, if necessary, removing the hydroxyl-protecting groups, to obtain the compound of the formula II. This process can be conducted in the same manner as the first and second steps of the process D to obtain the desired compound of the formula II.

Now, the present invention will be described in further detail with reference to Examples. However, it should be understood that the present invention is by no means restricted to such specific Examples.

EXAMPLE 1

N benzyl-5,6-dimethoxy-N-methylisoindolinium chloride 1.33 g (11 mmol) of N-benzylmethylamine and 2.07 g (15 mmol) of potassium carbonate were suspended in 24 ml of acetone, and 2.35 g (10 mmol) of 4,5-bis(chloromethyl)veratrol was added thereto at room temperature. The mixture was stirred for 18 hours. After cooling, the precipitate was collected by filtration, washed with 10 ml of acetone and dried in air to obtain 5.03 g (purity: 53%) of a white powder of the above identified compound containing inorganic substance. This powder was dissolved in 20 ml of water. Then, the solution was adjusted to pH 2.8 with 2N hydrochloric acid and subjected to HP-20 (50 ml). Elution was conducted with water, and a fraction containing the desired product was collected. The solvent was distilled off, and 10 ml of acetone was added to the oily residue. The mixture was left to stand overnight. The precipitated crystals were collected by filtration and washed with 10 ml of acetone to obtain 720 mg of the above identified compound as colorless needle crystals.

m.p.: 212° C.

IR(KBr)cm$^{-1}$: 3100-2700, 1610, 1505, 1460, 1330, 1220, 1100, 990, 925, 760, 700.

NMR(DMSO-d$_6$)δ: 3.14(3H,s), 3.75(6H,s), 4.60(2H,d,J=13.7Hz), 5.06(2H,s), 5.15(2H,d,J=13.7Hz), 7.06(2H,s), 7.30-7.80(5H,m)

EXAMPLE 2

N-benzyl-5,6-dihydroxy-N-methylisoindolinium bromide

To 1.0 g (3.13 mmol) of N-benzyl-5,6-dimethoxy-N-methylisoindolinium chloride, 10 ml of 48% hydrobromic acid was added, and the mixture was heated at reflux for 3 hours at an external temperature of from 110° to 130° C. The reaction solution was evaporated to dryness under reduced pressure, and the crystal residue was washed with 10 ml of acetone to obtain 1.05 g of the above identified compound.

m.p.: 229° C. (decomposed).

IR(KBr)cm$^{-1}$: 3600-2250, 1620, 1515, 1455, 1335, 1215, 1155, 1090, 925, 865, 770, 700.

NMR(DMSO-d$_6$)δ: 3.03(3H,s), 4.48(2H,d,J=13.7Hz), 4.89(2H,s), 4.97(2H,d,J=13.7Hz), 6.79(2H,s), 7.40-7.70(5H,m), 9.14(2H,br).

EXAMPLE 3

N-benzyl-5,6-dimethoxy-N-methylisoindolinium iodide 500 mg (1.86 mmol) of N-benzyl-5,6-dimethoxyisoindoline was dissolved in 10 ml of acetone, and 316 mg (2.27 mmol) of methyl iodide was added thereto at room temperature. The mixture was left to stand for 6 hours. Then, the precipitated crystals were collected by filtration and washed with 10 ml of acetone to obtain 640 mg of the above identified compound. The filtrate was distilled off under reduced pressure, and the crystal residue was washed with 10 ml of ethyl acetate to obtain 110 mg of the secondary crystals. The total yield was 750 mg.

m.p.: 177° C. (decomposed).

IR(KBr)cm$^{-1}$: 3510, 3370, 3100–2800, 1615, 1510, 1460, 1335, 1220, 1100, 990, 765, 700, 500.

NMR(DMSO-d$_6$)δ: 3.10(3H,s), 3.77(6H,s), 4.60(2H,d,J=13.7Hz), 4.89(2H,s), 5.06(2H,d,J=13.7Hz), 7.07(2H,s), 7.40–7.75(5H,m).

EXAMPLE 4

N-benzyl-5,6-dihydroxy-N-methylisoindolinium bromide

To 10 g (24.3 mmol) of N-benzyl-5,6-dimethoxy-N-methylisoindolinium iodide, 50 ml of 48% hydrobromic acid was added, and the mixture was heated at reflux for 3 hours at an external temperature of 120° C. The reaction solution was evaporated to dryness under reduced pressure, and the crystal residue was washed with 20 ml of acetone to obtain 6.90 g of the above identified compound. The filtrate was left to stand overnight, to obtain 190 mg of the secondary crystals. The total yield was 7.09 g. The melting point, the infrared absorption spectrum and the $^1$H-NMR spectrum of this product agreed to those of Example 2.

EXAMPLE 5

N-benzyl-5,6-dihydroxy-N-methylisoindolinium iodide 590 mg (2.44 mmol) of N-benzyl-5,6-dihydroxyisoindoline was dissolved in 10 ml of acetone, and 0.16 ml (2.5 mmol) of methyl iodide was added thereto at room temperature. The mixture was left to stand for 4 hours, and the precipitated crystals were collected by filtration and washed with 10 ml of acetone to obtain 733 mg of the above identified compound.

m.p.: 192° C. (decomposed).

IR(KBr)cm$^{-1}$: 3600-3400, 1710, 1610, 1510, 1465, 1320, 1140, 1080, 920, 860, 775, 710.

NMR(DMSO-d$_6$)δ: 3.04(3H,s), 4.48(2H,d,J=13.7Hz), 4.87(2H,s), 4.96(2H,d,J=13.7Hz), 6.80(2H,s), 7.35–7.80(5H,m).

EXAMPLE 6

N-benzyl-5,6-dimethoxyisoindoline 2.35 g (10 mmol) of 4,5-bis(chloromethyl)veratrol was added at room temperature to a suspension comprising 5 ml of a 50% sodium hydroxide aqueous solution, 25 ml of toluene, 1.25 g (11.66 mmol) of benzylamine and 0.2 g of Starks catalyst (a 90% aqueous solution), and the mixture was stirred for 20 hours. The organic layer was separated, dried over anhydrous sodium sulfate and concentrated to dryness under reduced pressure. The crystal residue was washed with diisopropyl ether to obtain 1.87 g of the above identified compound as colorless needle crystals.

m.p.: 111° C.

IR(KBr)cm$^{-1}$: 3100–2700, 1610, 1500, 1465, 1340, 1325, 1280, 1215, 1185, 1100, 990, 845, 835, 760, 695, 485.

NMR(CDCl$_3$)δ: 3.73(6H,s), 3.88(6H,s) 6.70(2H,s), 7.20–7.45(5H,m).

EXAMPLE 7

N-benzyl-5,6-dihydroxyisoindoline hydrobromide

To 5.38 g (20 mmol) of N-benzyl-5,6-dimethoxyisoindoline, 50 ml of 48% hydrobromic acid was added, and the mixture was heated at reflux for 5 hours at an external temperature of from 110° to 125° C. After cooling, the precipitated crystals were collected by filtration and washed with 5 ml of water and 10 ml of acetone to obtain 6.36 g of the above identified compound as a grayish white powder. The powder was dissolved in 150 ml of hot water, and the solution was subjected to decolorization with 1.0 g of active carbon and then cooled with ice to obtain 4.75 g of prism crystals.

m.p.: 153° C. (decomposed).

IR(KBr)cm$^{-1}$: 3500–2000, 1620, 1515, 1455, 1340, 1215, 1085, 925, 865, 770.

NMR(DMSO-d$_6$)δ: 4.42(4H,s), 4.59(2H,s) 6.75(2H,s), 7.30–7.70(5H,m), 8.70–9.70(2H,br), 10.70–11.40(1H,br s).

EXAMPLE 8

N-benzyl-5,6-dihydroxyisoindoline 1.0 g (3.1 mmol) of N-benzyl-5,6-dihydroxyisoindoline hydrobromide was dissolved in 40 ml of a 50% methanol aqueous solution, and the solution was adjusted to pH 8.0 with 8% aqueous ammonia. The precipitated crystals were collected by filtration and washed with 5 ml of cold water and 5 ml of cold acetone to obtain 640 mg of the above identified compound.

m.p.: 188° C. (decomposed).

IR(KBr)cm$^{-1}$: 3490, 2800, 1605, 1510, 1470, 1340, 1300, 1210, 1150, 850, 770, 700.

NMR(DMSO-d$_6$)δ: 3.67(4H,s), 3.77(2H,s) 6.58(2H,s), 7.31(5H,s).

EXAMPLE 9

5,6-Dimethoxy-N-methylisoindoline 1.33 g (11 mmol) of N-benzylmethylamine and 2.07 g (15 mmol) of potassium carbonate were suspended in 24 ml of acetone, and 2.35 g (10 mmol) of 4,5-bis(chloromethyl)veratrol was added thereto at room temperature. The mixture was stirred for 22 hours. After cooling, the precipitate was collected by filtration, washed with 10 ml of acetone and dried in air to obtain 4.96 g (purity: about 55%) of a white powder of N-benzyl-5,6-dimethoxy-N-methylisoindolinium chloride containing inorganic substance. The white powder was suspended in 50 ml of methanol, and the suspension was stirred for 10 minutes. Then, the insoluble substances were filtered off. To the filtrate, 2 ml of 6N hydrochloric acid and 300 mg of a 10% palladium carbon catalyst were added, and the catalytic reduction was conducted for 5 hours in a hydrogen gas stream. After filtering off the catalyst, the filtrate was concentrated to dryness under reduced pressure. To the residue, 20 ml of water was added, and the mixture was adjusted to strongly alkaline by an addition of a 50% sodium hydroxide aqueous solution and then extracted twice with benzene. The extract solution was dried over anhydrous sodium sulfate, and the solvent was distilled off to obtain 1.61 g (yield of 83.4% from 4,5-bis(chloromethyl)veratrol) of 5,6-dimethoxy-N-methylisoindoline.

m.p.: 80° C.

IR(KBr)cm$^{-1}$: 2940, 2860, 2830, 2745, 1605, 1500, 1450, 1345, 1225, 1190, 1095, 835.

NMR(DMSO-d$_6$)δ: 2.45(3H,s), 3.74(10H,s) 6.82(2H,s).

EXAMPLE 10

5,6-Dimethoxy-N-methylisoindoline hydrochloride 1.0 g (3.12 mmol) of N-benzyl-5,6-dimethoxy-N-methylisoindolinium hydrochloride was dissolved in 20 ml of methanol, and 0.5 ml of 6N hydrochloric acid and 100 mg of a 10% palladium carbon catalyst were added thereto. The catalytic reduction was conducted at room temperature for 5 hours in a hydrogen gas stream. The catalyst was filtered off, and the solvent was distilled off under reduced pressure. The crystal residue was washed with 10 ml of acetone to obtain 650 mg of the above identified compound.

m.p.: 233° C. (decomposed).

IR(KBr)cm$^{-1}$: 2940, 2790-2200, 1615, 1505, 1460, 1335, 1280, 1220, 1095, 990, 830.

NMR(DMSO-d$_6$)δ: 2.94(3H,s), 3.74(6H,s) 4.46(4H,s), 6.99(2H,s).

EXAMPLE 11

5,6-Dimethoxy-N-methylisoindoline 1.0 g (2.43 mmol) of N-benzyl-5,6-dimethoxy-N-methylisoindolinium iodide was dissolved in 40 ml of a 50% methanol aqueous solution, and 300 mg of a 10% palladium carbon catalyst was added. Then, the catalytic reduction was conducted at 50° C. for 6 hours in a hydrogen gas stream. After filtering off the catalyst, methanol was distilled off under reduced pressure, and the residual solution was adjusted to strongly alkaline by an addition of a 50% sodium hydroxide aqueous solution. Then, the solution was extracted twice with methylene chloride. The extract solution was dried over anhydrous sodium sulfate, and the solvent was distilled off to obtain 200 mg of the above identified compound.

m.p.: 80° C.

IR(KBr)cm$^{-1}$: 2940, 2860, 2830, 2745, 1605, 1500, 1450, 1345, 1225, 1190, 1095, 835.

NMR(DMSO-d6)δ: 2.45(3H,s), 3.74(10H,s) 6.82(2H,s).

EXAMPLE 12

5,6-Dihydroxy-N-methylisoindoline hydrobromide 1.0 g (2.97 mmol) of N-benzyl-5,6-dihydroxy-N-methylisoindolinium bromide obtained in Example 4 was dissolved in a solution comprising 10 ml of methanol and 10 ml of acetic acid, and 300 mg of a 10% palladium carbon catalyst was added thereto. Then, the catalytic reduction was conducted at 60° C. for 6 hours in a hydrogen gas stream. After filtering off the catalyst, the filtrate was evaporated to dryness under reduced pressure. To the residue, 10 ml of methanol was added, and the mixture was left to cool. The precipitated crystals were collected by filtration and washed with 10 ml of acetone to obtain 500 mg of the above identified compound as white crystals.

m.p.: 216°-219° C. (decomposed).

IR(KBr)cm$^{-1}$: 3700-2450, 1615, 1515, 1465, 1455, 1330, 1290, 1185, 860, 640.

NMR(DMSO-d$_6$)δ: 2.96(3H,s), 4.05-4.90(4H,br) 6.77(2H,s), 10.93(2H,br).

REFERENCE EXAMPLE

4,5-Bis(chloromethyl)veratrole

In 1,800 ml of dioxane, 124.4 g (0.9 mol) of veratrole and 135 g (4.5 mol) of pulverized paraformaldehyde were suspended, and hydrogen chloride gas was passed through the reaction solution for 2 hours under cooling with ice.

The reaction solution was left to stand at 5° C. for 7 days to complete the reaction, and the solvent was distilled off under reduced pressure. To the residue thus obtained, 400 ml of methylene chloride was added, and the insoluble substances were filtered off. The solvent was distilled off under reduced pressure, and the crystal residue thus obtained was washed three times with 200 ml of hexane to obtain 194.6 g of the above identified compound.

m.p.: 85°-86.5° C.

IR(KBr)cm$^{-1}$: 1605, 1520, 1460, 1445, 1360, 1270, 1235, 1145, 1100, 1000, 870, 660, 645.

NMR(CDCl$_3$)δ: 3.89(6H,s), 4.69(4H,s), 6.87(2H,s).

According to the present invention, it is possible to readily produce in good yield an N,N-disubstituted 5,6-disubstituted isoindolinium derivative from a 4,5-bis(halomethyl)catechol derivative or an N-substituted 5,6-disubstituted isoindoline derivative as the starting material, or to readily produce in good yield an N-substituted 5,6-disubstituted isoindoline derivative from a 4,5-bis(halomethyl)catechol derivative, an N-substituted 5,6-disubstituted isoindoline derivative or an N,N-disubstituted 5,6-disubstituted isoindolinium derivative as the starting material.

The compounds of the present invention are useful as intermediates for the preparation of cephalosporin derivatives (bactericidal agents, U.S. Pat. No. 4,677,100) represented by the formula:

$$\text{acyl-NH} \underset{O}{\overset{S}{\underset{\Big|}{\bigsqcup}}} \underset{COO^{\ominus}}{\overset{}{\underset{N}{\bigsqcup}}} CH_2^{\oplus}N\underset{CH_3}{\overset{}{\bigsqcup}} \underset{}{\overset{OR}{\underset{OR}{\bigsqcup}}}$$

wherein R is a hydrogen atom or an alkanoyl group, and acyl is an acyl group, which have a (5,6-dihydroxy-N-methyl-2-isoindolinio)methyl group or a (5,6-dialkanoyl-N-methyl-2-isoindolinio)methyl group such as a (5,6-diacetoxy-N-methyl-2-isoindolinio)methyl group, at the 3-position of the cephem nucleus.

We claim:

1. A compound having the formula:

$$R^3O\underset{R^3O}{\overset{}{\bigsqcup}} \overset{R^4}{\underset{N^{\oplus}}{\bigsqcup}} .X^{\ominus} \underset{R^5}{}$$
(II)

wherein R$^3$ is a hydrogen atom or a hydroxyl-protecting group selected from the group consisting of an acetyl group, a methyl group, a benzyl group and an ethoxycarbonyl group, or two R$^3$ of vicinal —OR$^3$ groups together form a methylene group, an ethylene group, a benzylidene group, a methoxymethylidene group, a methoxyethylidene group, an isopropylidene group or a carbonyl group, $R^4$ and $R^5$ which may be the same or different are N-protecting groups selected from the group consisting of lower alkyl groups and $C_{7-12}$ aralkyl groups selected from the group consisting of benzyl, 3-methoxybenzyl, 4-methoxybenzyl, 3,4-dimethoxybenzyl, α-methylbenzyl, phenethyl, 3-phenylpropyl, 1-naphthylmethyl and diphenylmethyl, and $X^{\ominus}$ is an anion selected from the group consisting of halide, sulfate, hydrogen sulfate, methylsulfate, p-toluenesulfonate, methanesulfonate and trifluoroacetate.

2. The compound according to claim 1, which has the formula:

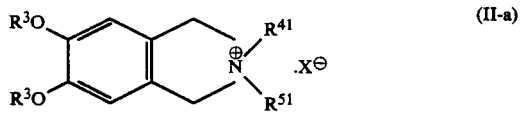

(II-a)

wherein $R^3$ and $X^{\ominus}$ are as defined in claim 1, and $R^{41}$ and $R^{51}$ which may be the same or different are N-protecting groups selected from the group consisting of $C_{1-4}$ alkyl groups and $C_{7-12}$ aralkyl groups.

3. The compound according to claim 2, wherein each of $R^{41}$ and $R^{51}$ which may be the same or different is a methyl group, an ethyl group, a propyl group, an isopropyl group, a butyl group, an isobutyl group, a sec-butyl group, a tert-butyl group, a benzyl group, a 3-methoxybenzyl group, a 4-methoxybenzyl group, a 3,4-dimethoxybenzyl group, a diphenylmethyl group, an α-methylbenzyl group, a phenethyl group, a 3-phenylpropyl group or a 1-naphthylmethyl group.

4. The compound according to claim 1, which has the formula:

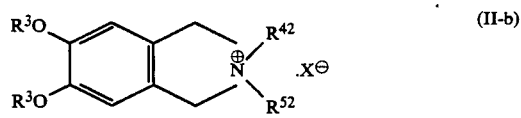

(II-b)

wherein $R^3$ and $X^{\ominus}$ are as defined in claim 1, and $R^{42}$ and $R^{52}$ which may be the same or different are $C_{1-4}$ alkyl groups.

5. The compound according to claim 4, wherein each of $R^{42}$ and $R^{52}$ which may be the same or different is a methyl group, an ethyl group or a propyl group.

6. The compound according to claim 1, which has the formula:

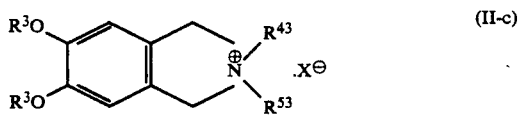

(II-c)

wherein $R^3$ and $X^{\ominus}$ are as defined in claim 1, and $R^{43}$ and $R^{53}$ which may be the same or different are $C_{7-12}$ aralkyl groups.

7. The compound according to claim 6, wherein each of $R^{43}$ and $R^{53}$ which may be the same or different is a benzyl group, a 3-methoxybenzyl group, a 4-methoxybenzyl group, a 3,4-dimethoxybenzyl group, a diphenylmethyl group, an α-methylbenzyl group, a phenethyl group, a 3-phenylpropyl group or a 1-naphthylmethyl group.

8. The compound according to claim 1, which has the formula:

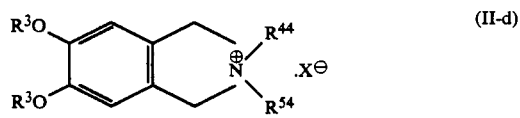

(II-d)

wherein $R^3$ and $X^{\ominus}$ are as defined in claim 1, $R^{44}$ is a $C_{1-4}$ alkyl group, and $R^{54}$ is a $C_{7-12}$ aralkyl group.

9. The compound according to claim 8, wherein $R^{44}$ is a methyl group, an ethyl group, a propyl group, an isopropyl group, a butyl group, an isobutyl group, a sec-butyl group of a tert-butyl group, and $R^{54}$ is a benzyl group, a 3-methoxybenzyl group, a 4-methoxybenzyl group, a 3,4-dimethoxybenzyl group, a diphenylmethyl group, an α-methylbenzyl group, a phenethyl group, a 3-phenylpropyl group of a 1-naphthylmethyl group.

* * * * *